(12) United States Patent
Furrer et al.

(10) Patent No.: US 7,880,011 B2
(45) Date of Patent: Feb. 1, 2011

(54) AMIDE ADDITION REACTION

(75) Inventors: Stefan Michael Furrer, Cincinnati, OH (US); David C. Bom, Cincinnati, OH (US); David Max Dastrup, Liberty Township, OH (US); Ioana Maria Ungureanu, Cincinnati, OH (US)

(73) Assignee: Givandan, S.A., Vernier (CH)

( * ) Notice: Subject to any disclaimer, the term of this patent is extended or adjusted under 35 U.S.C. 154(b) by 0 days.

(21) Appl. No.: 12/173,447

(22) Filed: Jul. 15, 2008

(65) Prior Publication Data
US 2009/0030042 A1 Jan. 29, 2009

Related U.S. Application Data

(60) Provisional application No. 60/961,656, filed on Jul. 23, 2007.

(51) Int. Cl.
C07D 213/40 (2006.01)
(52) U.S. Cl. .................... 546/336; 546/337
(58) Field of Classification Search ........... 546/336, 546/337
See application file for complete search history.

(56) References Cited

U.S. PATENT DOCUMENTS

| | | | |
|---|---|---|---|
| 3,516,943 A | 6/1970 | Brynko et al. |
| 4,150,052 A | 4/1979 | Watson et al. |
| 4,285,984 A | 8/1981 | Huber |
| 5,759,599 A | 6/1998 | Wampler et al. |
| 6,039,901 A | 3/2000 | Soper et al. |
| 6,045,835 A | 4/2000 | Soper et al. |
| 6,056,949 A | 5/2000 | Menzi et al. |
| 6,106,875 A | 8/2000 | Soper et al. |
| 6,123,974 A | 9/2000 | Gautschi et al. |
| 6,222,062 B1 | 4/2001 | Anderson et al. |
| 6,306,818 B1 | 10/2001 | Anderson et al. |
| 6,325,859 B1 | 12/2001 | De Roos et al. |
| 6,325,951 B1 | 12/2001 | Soper et al. |
| 6,335,047 B1 | 1/2002 | Daniher et al. |
| 6,348,618 B1 | 2/2002 | Anderson et al. |
| 6,387,431 B1 | 5/2002 | Gautschi |
| 6,426,108 B1 | 7/2002 | Gautschi |
| 6,436,461 B1 | 8/2002 | Bouwmeesters et al. |
| 6,440,912 B2 | 8/2002 | McGee et al. |
| 6,451,366 B1 | 9/2002 | Daniher et al. |
| 6,482,433 B1 | 11/2002 | DeRoos et al. |
| 6,610,346 B1 | 8/2003 | Acuna et al. |
| 6,689,740 B1 | 2/2004 | McGee et al. |
| 6,805,893 B2 | 10/2004 | Acuna et al. |
| 6,869,923 B1 | 3/2005 | Cunningham et al. |
| 2001/0008635 A1 | 7/2001 | Quellet et al. |
| 2002/0081370 A1 | 6/2002 | Daniher et al. |
| 2003/0082272 A1 | 5/2003 | Bouwmeesters et al. |
| 2003/0165587 A1 | 9/2003 | Binggeli et al. |
| 2004/0047960 A1 | 3/2004 | Acuna et al. |
| 2005/0214337 A1 | 9/2005 | McGee et al. |
| 2005/0227906 A1 | 10/2005 | Schudel et al. |
| 2005/0233042 A1 | 10/2005 | Galopin et al. |
| 2006/0035008 A1 | 2/2006 | Virgallito et al. |
| 2006/0276667 A1 | 5/2006 | Galopin et al. |
| 2006/0154850 A1 | 7/2006 | Quellet et al. |
| 2006/0172917 A1 | 8/2006 | Vedantam et al. |

FOREIGN PATENT DOCUMENTS

| | | |
|---|---|---|
| GB | 1351761 | 5/1974 |
| GB | 1351762 | 5/1974 |
| WO | WO01/03825 A1 | 1/2001 |
| WO | WO 2004/034791 A1 | 4/2004 |
| WO | WO 2005/049553 A1 | 6/2005 |
| WO | WO 2006/056096 A1 | 6/2006 |
| WO | WO 2007/019719 A1 | 2/2007 |

OTHER PUBLICATIONS

Magnus, G., et al., "The Pyridylethylation of Active Hydrogen Compounds V. The Reaction of Ammonia, Certain Amines, Amides and Nitriles With 2-and 4-Vinylpyricdine and 2-Methyl-5-Vinylpyridine", Journal of American Chemical Society, Aug. 20, 1956, pp. 4127-4129, vol. 78, American Chemical Society, Washington, D.C., U.S.

PCT/CH2008/000325-International Search Report, Sep. 29, 2008.

*Primary Examiner*—Janet L Andres
*Assistant Examiner*—David E Gallis
(74) *Attorney, Agent, or Firm*—Curatolo Sidoti Co., LPA; Joseph G. Curatolo; D. Ari Sherwin

(57) ABSTRACT

A method of making a compound of formula II

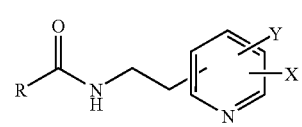

comprising the reaction of a compound of formula RCONH₂ with a compound of formula III

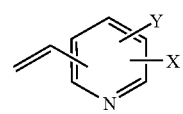

R being a moiety having between 1 and 15 carbon atoms and optionally from 1 to 5 heteroatoms independently selected from oxygen, nitrogen and sulfur, and X and Y being independently selected front the group consisting of H, methyl, ethyl, OMe, OEt, and mixtures thereof; the reaction being performed in a solvent in the presence of a base.

The method is useful for the inexpensive manufacture of certain commercially-valuable compounds, including some that have desirable cooling properties.

13 Claims, No Drawings

AMIDE ADDITION REACTION

This application claims the benefits of the filing date of U.S. Provisional Application for Patent Ser. No. 60/961,656, filed Jul. 23, 2007, incorporated herein by reference.

This disclosure relates to the addition of carboxamides to vinyl pyridines.

N-substituted p-menthane carboxamides are well known in the art as compounds that impart a cooling sensation to the skin or the mucous membranes of the body. Typical examples of such compounds are described in, for example, British Patent GB 1,421,744.

In International Application PCT/CH2006/000427 there are disclosed compounds of the general formula I

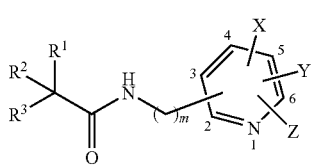

I in which X, Y, Z, $R^1$, $R^2$, $R^3$ and m are as defined in that document. In particular examples, at least two of $R^1$, $R^2$, $R^3$ together form a cyclic radical.

These compounds have usually been prepared by the reaction of a menthane carboxylic acid chloride with a suitable monoamine. One example of this is the following reaction:

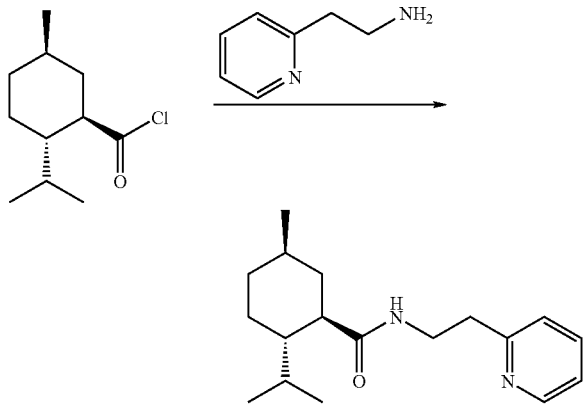

Although efficient, this reaction involves the use of expensive materials.

It has now been found that it is possible to prepare such compounds by a simple, inexpensive process. There is therefore provided a method of making a compound of formula II

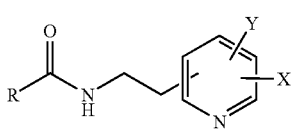

II comprising the reaction of a compound of the formula $RCONH_2$ with a compound of formula III

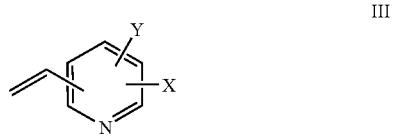

III

R being a moiety having between 1 and 15 carbon atoms and optionally from 1 to 5 heteroatoms independently selected from oxygen, nitrogen and sulfur, and X and Y being independently selected from the group consisting of H, methyl (Me), ethyl (Et), OMe, OEt and mixtures thereof;

the reaction being performed in a solvent in the presence of a base.

There is also provided a compound of the formula II as hereinabove defined, prepared by a process as hereinabove defined.

The compounds of formula III are vinyl pyridines, optionally substituted. Either the 2- or the 4-vinyl pyridine or derivatives thereof may be used.

The solvent may be any suitable solvent. It may be capable of dissolving all the reactants and the reaction product. Useful solvents include oxygen- and nitrogen-containing non-reactive solvents and aromatic hydrocarbons. Non-limiting examples of solvents include xylene, toluene, dimethyl formamide and tetrahydrofuran (THF).

The quantity of solvent present is any suitable quantity.

The base for use in the process may be any suitable base. Typical examples of suitable bases include sodium methoxide, potassium tert-butoxide, lithium diisopropyl amine, sodium hydride, sodium hydroxide and potassium hydroxide. A acceptable concentration range is from about 0.01 to about 0.5 equivalents.

Particular examples of bases include sodium hydroxide, potassium hydroxide and potassium tert-butoxide. These may be used at concentration ranges of from about 0.05 to about 0.25 equivalents.

In particular embodiments involving the use of sodium or potassium bases, the mixture may comprise a chelating agent. This permits higher yields and faster reaction limes. Examples of suitable chelating agents include crown ethers, such as 18-crown-6, particularly in combination with bases such as potassium, hydroxide and potassium tert-butoxide.

Alternatively, the solvent itself may be selected such that it has chelating properties. If such solvents are used, a separate chelating agent may be used in a reduced quantity or even omitted altogether. Solvents that are useful in this regard include dimethyl formamide (DMF), N-methylpyrrolidone (NMP). Combinations of all or any these solvents may be used in any desired proportions.

In a particular embodiment, the reaction is heated or performed under pressure, for example, in a bomb or in a sealed microwave vessel. While it is generally not essential to do this, the use of such measures can lead to higher yields and faster reaction times. A particular temperature range for heating is at least about 50° C., more particularly from about 100° to about 200° C. Naturally, the use of higher temperatures will have an effect on the selection of solvent, but the skilled person will be able to select suitable solvents for each case.

Particular embodiments of the compound are those in which R is selected according to the description hereinafter provided.

In particular embodiments, R is selected from arylalkenyl, heteroarylalkenyl, arylalkyl, heteroarylalkyl, alkyl, alkoxyalkyl, alkenyl, cycloalkyl, cycloalkenyl, aryl and heteroaryl moieties, and mixtures thereof.

Particular examples of R include (but are not limited to) 2,4-dimethylpent-3-yl, 2,3,4-dimethylpent-3-yl, adamantyl and 2-isopropyl-5-methyl-cyclohexyl-1-yl (in particular embodiments, the (1R, 2S, 5R) form).

In a certain embodiment, the process is particularly useful for producing the compounds of International Application PCT/CH2006/000427 hereinabove described. In such a case, R is a moiety of formula IV

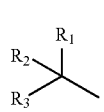

IV in which $R_1$, $R_2$ and $R_3$ together comprise at least 6 carbons, and are selected such that
(a) (i) $R_1$ is selected from the group consisting of H, Me, Et, isopropyl and $C_4$-$C_5$ branched alkyl; and
  (ii) $R_2$ and $R_3$ are independently selected from the group consisting of Me, Et, isopropyl and $C_4$-branched alkyl; or
(b) any two or all of $R_1$, $R_2$ and $R_3$ together form a monocyclic, bicyclic or tricyclic radical having up to 10 carbons.

Examples of cyclic radicals as described under (b) above include 3-para-menthyl, bornyl and adamantyl.

A particular example of Formula IV is 2-isopropyl-5-methyl-cyclohexyl-1-yl (in a particular embodiment, the (1R, 2S, 5R) variant).

The method is now described with reference to the following non-limiting examples.

EXAMPLE 1

Preparation of N-(2-pyridin-2-ylethyl)p-menthanecarboxamide[(1R,2S,5R)-2-isopropyl-5-methyl-N-(2-(pyridin-2-yl)ethyl)cyclohexanecarboxamide]

In a 15 mL round bottom flask, fitted with magnetic stirrer and reflux condensor, 0.368 g of p-menthanecarboxamide, 4 mL of toluene, 0.32 mL of 2-vinyl pyridine, 0.027 g of 18-crown-6 and 0.12 ml, of potassium tert-butoxide (20% in THF) were added. The mixture was heated at 110° C. for 3 hours, yielding 97% conversion by GC.

EXAMPLE 2

Preparation of N-(2-pyridin-2-ylethyl)p-menthanecarboxamide[(1R,2S,5R)-2-isopropyl-5-methyl-N-(2-(pyridin-2-yl)ethyl)cyclohexanecarboxamide]

In a 5 mL Biotage microwave vial, fitted with magnetic stirrer, 0.1 g of p-menthanecarboxamide, 0.55 mL of toluene, 0.45 mL of NMP, 0.086 g of 2-vinyl pyridine and 3.1 mg of KOH were added. The vial was sealed and heated in the Biotage microwave instrument at 150° C. for 10 min, yielding 90.9% conversion by GC.

EXAMPLE 3

Preparation of N-(2-pyridin-2-ylethyl)p-menthanecarboxamide[(1R,2S,5R)-2-isopropyl-5-methyl-N-(2-yl)ethyl)cyclohexanecarboxamide]

In a 5 mL Biotage microwave vial, fitted with magnetic stirrer, 0.1 g of p-menthanecarboxamide, 1.0 mL of THF, 0.086 g of 2-vinyl pyridine and 0.1 eq. of potassium tert-butoxide (KOtBu) (20% in THF) were added. The vial was sealed and heated in the Biotage microwave instrument at 160° C. for 20 min, yielding 88% conversion by GC.

EXAMPLE 4

Preparation of N-(2-pyridin-2-ylethyl)p-menthanecarboxamide[(1R,2S,5R)-2-isopropyl-5-methyl-N-(2-(pyridin-2-yl)ethyl)cyclohexanecarboxamide]

In a 5 mL Biotage microwave vial, fitted with magnetic stirrer, 0.1 g of p-menthanecarboxamide, 1.0 mL of NMP, 0.086 g of 2-vinyl pyridine and 0.1 eq. of KOtBu (20% in THF) were added. The vial was sealed and heated in the Biotage microwave instrument at 150° C. for 10 min, yielding 95.3% conversion by GC.

EXAMPLE 5

Preparation of N-(2-pyridin-2-ylethyl)p-menthanecarboxamide[(1R,2S,5R)-2-isopropyl-5-methyl-N-(2-(pyridin-2-yl)ethyl)cyclohexanecarboxamide]

In a 5 mL Biotage microwave vial, fitted with magnetic stirrer, 0.1 g of p-menthanecarboxamide, 1.0 mL of NMP, 0.086 g, of 2-vinyl pyridine and 2.2 mg of NaOH were added. The vial was sealed and heated in the Biotage microwave instrument at 150° C. for 10 min, yielding 85.7% conversion by GC.

EXAMPLE 6

Preparation of N-(2-pyridin-2-ylethyl)p-menthanecarboxamide[(1R,2S,5R)-2-isopropyl-5-methyl-N-(2-(pyridin-2-yl)ethyl)cyclohexanecarboxamide]

In a 5 mL Biotage microwave vial, fitted with magnetic stirrer, 0.1 g of p-menthanecarboxamide, 0.05 mL of NMP, 0.95 mL of toluene, 0.082 mL of 2-vinyl pyridine and 3.1 mg of KOH were added. The vial was sealed and heated in the Biotage microwave instrument at 150° C. for 10 min, yielding 74.6% conversion by GC.

EXAMPLE 7

Preparation of N-(2-pyridin-2-ylethyl)p-menthanecarboxamide[(1R,2S,5R)-2-isopropyl-5-methyl-N-(2-(pyridin-2-yl)ethyl)cyclohexanecarboxamide]

In a 100 mL round bottom flask, fitted with magnetic stirrer and reflux stirrer, 5.0 g of p-menthanecarboxamide, 10 mL of NMP, and 150 mg of KOH were added. The mixture was heated for 1 hour at 120° C.

The mixture was cooled to room temperature and 60 mL of water were added slowly under stirring, while crystals separated from the mixture. The mixture was cooled to 0° C., filtered and the crystals were washed limes with ice cold water. The crude product was re-crystallized from ethyl acetate and hexane, yielding 3.96 g of white crystals (50% yield).

MS: 288 ([M$^{+\bullet}$]), 273, 245, 149, 121, 95

$^1$H NMR (300 MHz; DMSO) δ: 8.53 (d, 1H), 7.62 (td, 1H), 7.16 (m, 2H), 6.43 (s, 1H), 3.67 (nontuplet, 2H), 3.00 (t, 2H), 1.95 (td, 1H), 1.84-1.53 (m, 4H), 1.47 (broad t, 1H), 1.4-1.1 (m, 2H), 0.87 (d, 3H), 0.84 (d, 3H), 0.66 (d, 3H)

$^{13}$C NMR (75 MHz; DMSO) δ: 175.8, 159.7, 148.9, 136.7, 123.6, 121.55, 49.8, 44.3, 39.4, 38.35, 36.9, 34.6, 32.3, 28.55, 23.9, 22.3, 21.3, 15.95

EXAMPLE 8

Preparation of N-(4-pyridin-2-ylethyl)p-menthanecarboxamide[(1R,2S,5R)-2-isopropyl-5-methyl-N-(2-(pyridin-4-ethyl)cyclohexanecarboxamide]

In a 5 mL Biotage microwave vial, fitted with magnetic stirrer, 0.1 g of p-menthanecarboxamide, 1 mL of NMP, 0.082 mL of 4-vinyl pyridine and 3.1 mg of KOH were added. The vial was sealed and heated in the Biotage microwave instrument at 150° C. for 10 min, yielding 54% conversion by GC.

MS: 260 ([M$^{+\cdot}$]), 217, 149, 121, 95

EXAMPLE 9

Preparation of 2-isopropyl-2,3-dimethyl-N-(2-(pyridin-2-yl)ethyl)butanamide

In a 20 mL Biotage microwave vial, fitted with magnetic stirrer, 1.0 g of 2-isopropyl-2,3-dimethylbutanamide, 10 mL of toluene, 1.0 g of 2-vinyl pyridine, 0.027 g of 18-crown-6 and 0.18 g of potassium tert-butoxide (20% in THF) were added. The vial was sealed and heated in the Biotage microwave instrument at 200° C. for 30 min.

The mixture was acidified with 100 mL of HCl (1N in water) and 2 times extracted with MTBE. The aqueous layer was treated with 150 mL of NaOH (1N in water) and extracted 2 times with MTBE. The organic layer was dried over magnesium sulfate, concentrated and purified by column chromatography. 1.17 g of white crystals were obtained (70% yield).

Mp: 60-61° C.

MS: 262 ([M+]), 220, 205, 149, 121, 106, 93

$^1$H NMR (300 MHz; CDCl3) 8.53 (d, 1H), 7.63 (t, 1H), 7.16 (m, 2H), 6.69 (s, 1H), 3.67 (dd, 2H), 2.99 (t, 2H), 1.96 (m, 2H), 0.96 (s, 3H), 0.85 (d, 6H), 0.79 (d, 6H)

$^{13}$C (75 MHz; CDCL3) 175.6, 160.0, 149.1, 136.6, 123.4, 121.5, 51.4, 38.4, 36.9, 32.6, 18.1, 17.4, 14.1

EXAMPLE 10

Preparation of 2-phenyl-N-(2-(pyridin-2-yl)ethyl)butanamide

In a 10 mL Biotage microwave vial, fitted with magnetic stirrer, 2.5 g of 2-phenylbutyramide, 3 mL of NMP, 1.6 g of 2-vinyl pyridine, 0.1 g of KOH were added. The vial was sealed and heated in the Biotage microwave instrument at 150° C. for 10 min.

The mixture poured on ice, the pH was adjusted with NaOH (1N in water) to pH 12 and extracted with MTBE. The organic layer was washed with brine, dried over magnesium sulfate, concentrated and purified by column chromatography. 2.3 g of beige oil were obtained (56% yield).

MS: 266 ([M+]), 253, 240, 149, 121, 106, 91, 78, 65

$^1$H NMR (300 MHz; CDCl3) 8.40 (m, 1H), 7.50 (dt, 1H), 7.3-7.2 (m, 5H), 7.1 (dt, 1H), 7.0 (d, 1H), 6.35 (s, 1H), 3.60 (dd, 2H), 3.20 (t, 1H), 2.90 (t, 2H), 2.2-2.1 (m, 1H), 1.8-1.7 (m, 1H), 0.84 (t, 3H)

$^{13}$C (75 MHz; CDCl3) 173.5, 159.6, 149.1, 140.0, 136.5, 128.6, 128.1, 127.0, 123.4, 121.4, 55.4, 38.8, 36.8, 26.1, 12.3

EXAMPLE 11

Preparation of 2-(2-methoxybenzylamino)-N-(2-(pyridin-2-yl)ethyl)acetamide

In a 10 mL Biotage microwave vial, fitted with magnetic stirrer, 2.5 g of 2-(2-methoxybenzylamino)acetamide, 3 mL of NMP, 1.6 g of 2-vinyl pyridine, 0.1 g of KOH were added. The vial was sealed and heated in the Biotage microwave instrument at 150° C. for 10 min.

The mixture poured on ice, the pH was adjusted with NaOH (1N in water) to pH 12 and extracted with MTBE. The organic layer was washed with brine, dried over magnesium sulfate, concentrated and purified by column chromatography. 1.05 g of beige oil were obtained (27% yield).

MS: 299 ([M+]), 178, 164, 150, 136, 121, 106, 91, 78, 65, 51

$^1$H NMR (300 MHz; CDCl3) 8.50 (m, 1H), 7.80 (s, 1H), 7.6 (dt, 1H), 7.3-7.1 (m, 4H), 7.0-6.8 (m, 2H), 3.82 (s, 3H), 3.75-3.65 (m, 2H), 3.65 (s, 2H), 3.23 (s, 2H), 3.05 (t, 2H), 1.95 (s, 1H)

$^{13}$C (75 MHz; CDCL3) 171.8, 159.4, 157.6, 149.4, 136.4, 129.9, 128.6, 123.4, 121.5, 120.5, 110.3, 55.2, 51.8, 49.4, 38.3, 37.6

These examples are for the purpose of illustration only and it is understood that variations and modifications can be made by one skilled in the an without departing from the spirit and the scope of the invention. It should be understood that the embodiments described are not only in the alternative, but, can be combined.

We claim:

1. A method of making a compound of formula I

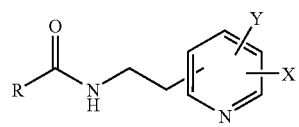

comprising reacting a compound of the formula RCONH$_2$, with a compound of formula III

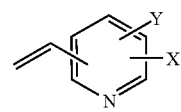

R being a moiety having between 1 and 15 carbon atoms and optionally from 1 to 5 heteroatoms independently selected from oxygen, nitrogen and sulfur, and X and Y being independently selected from the group consisting of H, methyl, ethyl, OMe, and OEt;

the reaction being performed in a solvent in the presence of a base, in which the base is selected from the group of sodium- and potassium-containing bases and the solvent comprises at least one chelating agent.

2. The method according to claim 1, in which the chelating agent is selected from the group consisting of solvents having chelating properties and separately-added chelating agents.

3. The method according to claim 2, in which the chelating agent is a crown ether.

4. The method according to claim 1, in which the reaction is performed under conditions selected from at least one of elevated temperature and elevated pressure.

5. The method according to claim 4, in which the elevated temperature is at least about 50° C.

6. The method according to claim 5, in which the elevated temperature lies within the range of about 100° to about 200° C.

7. The method according to claim 1, in which R is a moiety of formula IV

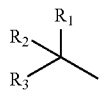

IV in which $R^1$, $R^2$ and $R^3$ together comprise at least 6 carbons, and in which
(a)(i) $R_1$ is selected from the group consisting of H, Me, Et, isopropyl, $C_4$-$C_5$ branched alkyl, and mixtures thereof; and
(ii) $R_2$ and $R_3$ are independently selected from the group consisting of Me, Et, isopropyl, and $C_4$-branched alkyl; or
(b) any two or all of $R_1$, $R_2$ and $R_3$ together form a monocyclic, bicyclic or tricyclic radical having up to 10 carbons.

8. The method according to claim 7, in which the monocyclic, bicyclic or tricyclic radical is selected from 3-paramenthyl, bornyl, and adamantyl.

9. The method according to claim 7, in which R is 2-isopropyl-5-methyl-cyclohexyl-1-yl, optionally in the (1R, 2S, 5R) form.

10. The method according to claim 1, in which R is a moiety selected from the group consisting of arylalkenyl, heteroarylalkenyl, arylalkyl, heteroarylalkyl, alkyl, alkoxyalkyl, alkenyl, cycloalkyl, cycloalkenyl, aryl, and heteroaryl.

11. The method according to claim 10, in which R is selected from the group of 2,4-dimethylpent-3-yl, 2,3,4-dimethylpent-3-yl, adamantyl, and 2-isopropyl-5-methyl-cyclohexyl-1-yl.

12. The method according to claim 11, in which R is 2-isopropyl-5-methyl-cyclohexyl-1-yl in the (1R, 2S, 5R) form.

13. The method according to claim 1, in which the base is selected from the group consisting of sodium hydroxide, potassium hydroxide, potassium tert-butoxide, and mixtures thereof.

* * * * *